(12) United States Patent
Pusch et al.

(10) Patent No.: US 6,383,148 B1
(45) Date of Patent: *May 7, 2002

(54) METHOD OF MEASURING A BODY REGION

(75) Inventors: Martin Pusch, Duderstadt (DE); Dave Reynolds, Middlesex (GB)

(73) Assignee: Otto Bock Orthopaedische Industrie Besitz-und Verwaltungs-Kommanditgesellschaft, Duderstadt (DE)

(*) Notice: Subject to any disclaimer, the term of this patent is extended or adjusted under 35 U.S.C. 154(b) by 0 days.

This patent is subject to a terminal disclaimer.

(21) Appl. No.: 09/550,022

(22) Filed: Apr. 14, 2000

(30) Foreign Application Priority Data

Apr. 15, 1999 (DE) .......................... 199 16 978

(51) Int. Cl.[7] .......................... A61B 5/103; A61B 5/117
(52) U.S. Cl. .......................... 600/587; 128/898
(58) Field of Search .......................... 600/587, 592, 600/594, 425, 476; 33/511, 512; 623/901; 128/898, 920, 922

(56) References Cited

U.S. PATENT DOCUMENTS

| | | | | |
|---|---|---|---|---|
| 4,670,892 A | * | 6/1987 | Abele et al. ................... 378/4 |
| 4,779,629 A | * | 10/1988 | West et al. ................... 600/587 |
| 4,786,925 A | * | 11/1988 | Landwehr ..................... 396/14 |
| 4,821,200 A | * | 4/1989 | Oberg .......................... 700/182 |
| 4,885,844 A | * | 12/1989 | Chun ............................. 33/15 |
| 5,457,325 A | * | 10/1995 | Huberty ................. 250/559.29 |
| 5,671,055 A | * | 9/1997 | Whittlesey et al. ......... 600/592 |
| 5,800,364 A | * | 9/1998 | Glennie et al. ............. 600/592 |
| 5,956,525 A | * | 9/1999 | Minsky .......................... 396/3 |

FOREIGN PATENT DOCUMENTS

WO    WO 97/14932 A1 * 4/1997

* cited by examiner

Primary Examiner—John P. Lacyk
Assistant Examiner—Charles Marmor, II
(74) Attorney, Agent, or Firm—Foley & Lardner

(57) ABSTRACT

A method of measuring a body region of a human body includes recording at least two images of the body region from different camera positions, from which the contour lines are ascertained, for example, as a contrast. Used for scaling the images is a reference object with a reference zone, to which the camera is set in a perpendicular or near perpendicular viewing direction by means fan angle-determining device. The reference zone can be defined, for example, by perpendicularly protruding fins. From the projected images of the contour line and the reference zone, an individual model of the outside surface of the body region is subsequently ascertained by means of the reference model. From this individual model a prosthesis or orthesis can be fabricated.

21 Claims, 3 Drawing Sheets

METHOD OF MEASURING A BODY REGION

BACKGROUND OF THE INVENTION

1. Field of the Invention

The invention relates to a method of measuring an object, advantageously a body region of the human body.

2. Related Art

Methods for measuring a body region of the human body are required in particular for the fabrication of prostheses, for example, for stumps of limbs, as well as ortheses or medical supporting elements, such as compression stockings, for example, in order to make possible an individual adaptation of the prosthesis or orthesis to the respective body region.

The measuring of the respective body region on the one hand requires high accuracy, in order that the prosthesis or orthesis subsequently fabricated on the basis of the measurement data offers a high degree of wearing comfort. On the other hand, the measuring of the body region should be possible in a sufficiently short time and with relatively low expenditure on equipment. In this way the patient can be measured in situ in a relatively short time and is consequently spared the need to travel to where there is special measuring equipment, possibly far away, and is spared a protracted period of time for carrying out the measuring operation.

It is known for this purpose to use, for example, measuring tapes to measure the body region. In this case, for example when dealing with a stump of a limb, not only the length but generally also a number of circumferential measurements have to be carried out, which nevertheless generally do not allow very great accuracy in the measuring procedure. It is also known to take impressions of the body regions concerned. However, such a method is complicated and laborious; furthermore, for the production of the prosthesis or orthesis, an impression of the body region first has to be transported to the respective manufacturer, which in addition to transportation costs may also cause a greater time delay.

SUMMARY OF THE INVENTION

It is therefore an object of the present invention to provide an improved method of measuring a body region, especially for fitting a prosthesis or orthesis. Another object of the present invention is to provide a method which makes an exact measurement of the body region possible with relatively little effort and in a relatively short time.

In accomplishing the foregoing objects, there has been provided according to one embodiment of the present invention, a method of measuring a body region of a human body comprising arranging a reference object, having a reference zone of a previously known length, and an angle-determining device in a fixed spatial relationship with the body region. A camera is arranged in a first camera position in a first viewing direction, perpendicular to the reference zone, to view the body region with the reference object, and a first image is recorded. A camera is arranged in a second camera position in a second viewing direction, perpendicular to the reference zone, to view the body region with the reference object, and a second image is recorded. A determination is performed of first and second reference distances, which correspond to distances of the reference object from the first and second camera positions, from the length of the reference zone and the projected images of the reference zone on the images. A contour line is determined extending in three-dimensional space for each image from the reference distances and the projected image of the contour line on the basis of a previously stored reference model. An individual model of the body region is determined from the contour lines and the reference model.

BRIEF DESCRIPTION OF THE DRAWINGS

Embodiments of the invention, serving as an examples, are illustrated schematically in the drawings, in which.

DETAILED DESCRIPTION OF THE PREFERRED EMBODIMENTS

Figure 1:
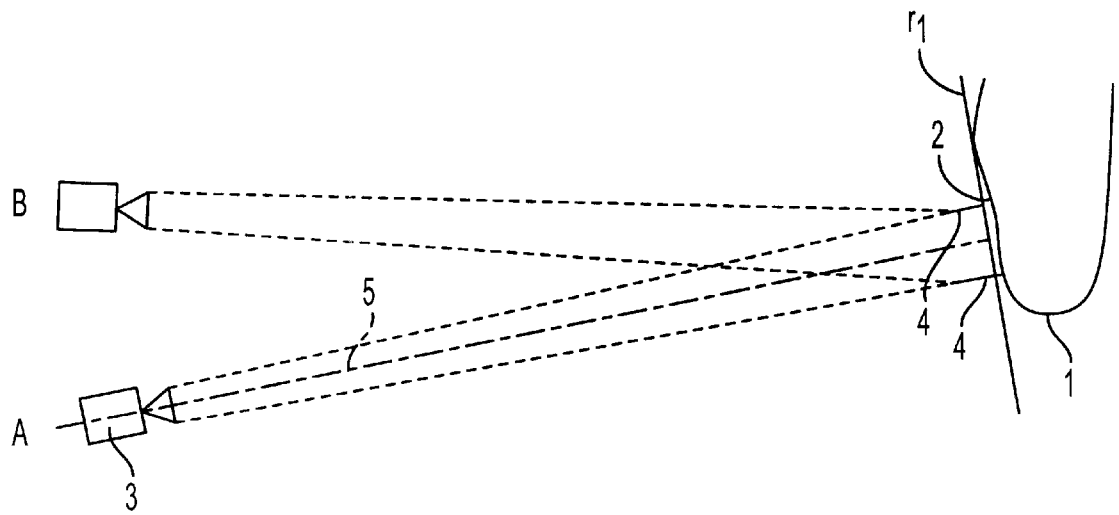
FIG. 1 shows a measuring arrangement for measuring a stump of a lower leg as a body region according to one embodiment of the invention.

The present invention relates to a method for measuring a body region of a human body. According to one embodiment of the present invention, a reference object with a reference zone of a previously known length and an angle-determining device is arranged in a fixed spatial relationship with the body region, for example, on the body region. A camera is arranged with the aid of the angle-determining device in a first camera position, in a first viewing direction, perpendicular to the reference zone, in which it picks up the body region with the reference object, and a first image is recorded. A camera is arranged with the aid of the angle-determining device in a second camera position, in a second viewing direction, perpendicular to the reference zone, in which it picks up the body region with the reference object, and a second image is recorded. The distances of the reference object from the camera positions are ascertained from the length of the reference zone and the projected images of the reference zone on the images as a first reference distance and second reference distance. A contour line, extending in three-dimensional space, is determined for each image from the reference distance and the projected image of the contour line on the basis of a previously stared reference model. An individual model of the body region is ascertained from the contour lines and the reference model.

Consequently, according to one embodiment of the invention, a reference model can be used for the body region concerned. The use of a reference model of this kind is generally possible with relatively high accuracy in the case of ortheses which support a body region, since the reference model stimulates a region of an at least largely intact body. Such a reference model is also appropriate when adapting prostheses with which a missing body part is being replaced, since the body region concerned, for example, the stump of a limb, is generally previously treated by operating techniques in a known way. For this purpose, the bones and muscles in particular are exposed at the respective locations of the body, in a largely known way.

Since, according to one embodiment of the invention, only one reference object is to be attached with a fixed spatial relationship to the body region concerned, in particular on the body region concerned, and at least two images of the body region concerned have to be recorded from different camera positions, the body region can be measured relatively quickly. Only the use of the reference object and one camera is necessary. The images can be subsequently sent, possibly even faxed, to the manufacturer of the prostheses or ortheses. The determination of the contour lines from the images and the calculation of an individual model of the body region by determination of the reference distances and on the basis of the reference model can, in this case, take place at the manufacturer's facility, so that, for example, complicated transportation of impressions or castings of the body region becomes superfluous.

According to another embodiment of the invention, the reference object has both a reference zone of a previously known length and an angle-determining device, for example, a visual angle-determining device, for setting the viewing direction, preferably the optical axis of the camera. Consequently, the camera can be positioned with the aid of the angle-determining device relatively simply in a direction perpendicular to the reference zone, without the body region to be measured having to be positioned or clamped in mounts or frameworks. The contour lines of the body region can be determined from a simple subsequent measuring procedure on the basis of the images recorded, without direct measuring or scanning of the body region in situ being necessary. Consequently, an individual model can be determined by computational ascertainment or computational adaptation. For determining the contour lines, the body region concerned may advantageously be brightly illuminated an recorded in front of a dark background. In particular, a contrast-improving, for example, lighter, coating may be placed or brushed over the body region, on which certain regions or locations may possibly also be marked. For example, a conventional computer programmed with appropriate software can be used to perform the computations according to the methods discussed herein.

Since, according to one embodiment of the invention, the distances of the camera from the reference object are ascertained from the images, it is unnecessary to undertake a complicated positioning of the body region at a fixed, predetermined distance from the camera, which would require the patient to keep still and nevertheless would generally lead to greater inaccuracy.

The reference object may advantageously be fastened, for example, adhesively attached, directly on the body region, so that there is a clear spatial relationship of the reference object to the body region. As a result, the patient can even move the body region concerned a little between the recordings, since a reference system of the body itself is defined by the reference object fastened on the body region, and this system is not changed fundamentally when there are movements of the body region.

The reference zone may be formed on the reference object in particular by two markings, the distance between which is previously known. The angle-determining device may be formed, for example, by one or two projections, which protrude perpendicularly from the linear scale and consequently ensure the perpendicular arrangement of the linear scale to the optical axis during alignment the viewing direction. The projections may advantageously serve at the same time as markings which are arranged at a known distance from one another. The projections may in this case also be displaceable on a rail, so that a distance can be preset.

The projections may be designed in particular as ribs, fins or blades which protrude perpendicularly from the linear scale. By making the side surfaces or upper sides and undersides of the projection or projections colored, a simple setting of the perpendicular viewing direction can be achieved by positioning the camera in such a way that the colored side surfaces are no longer detected, or only to a negligible extent.

By using the same camera for the various recordings, the expenditure on equipment for the measuring procedure is relatively low. Furthermore, in this case the various optical errors of different cameras, for example, a maladjustment of the optical axis, cannot have a cumulative effect. However, in principle, it is also possible for different cameras to be used.

The determination of the actual contour lines, extending in three-dimensional space, takes place according to one embodiment of the invention with the aid of the reference model. In an advantageous way, a reference plane in which the reference zone lies and which extends perpendicularly with respect to the viewing direction of the camera is firstly determined. The distance of this plane from the camera position consequently corresponds to the reference distance ascertained. The projected images of the contour lines may advantageously be related firstly to this reference plane. The position of the reference plane generally does not coincide with the actual position of the contour lines enveloping the body region. Subsequently, firstly the contour lines and from them the individual model are determined from the contour line projections and the reference distances.

Furthermore, for example, a prominent location or subregions of the body region which can be detected in at least one of the projected images could be used. Instead of such noticeable locations or subregions, it is correspondingly also possible to mark locations or subregions of the body region, in particular by marking on a coating of the body region. These noticeable or marked locations or subregions may be used in addition to the contour lines for determining the individual model. Consequently, an individual model can be ascertained from contour lines and further locations or subregions of the body region on the basis of a reference model.

The method according to the embodiments of the invention can be used in particular for measuring limbs, in particular stumps of limbs, such as the stump of a lower leg, for example, so that subsequent adaptation of a prosthesis is made possible. Furthermore, body regions such as a foot, for example, can also be measured, in order to make possible a subsequent adaptation of an orthesis, for example, compression stockings.

The aforementioned method of the present invention is illustrated in further detail by the exemplary embodiments illustrated in FIGS. 1–5. For example, as shown in FIG. 1, a reference scale or lattice 2, serving as a reference object, is fastened, for example, adhesively on a stump 1 of a lower leg as a body region to be measured. The alignment of the reference scale is performed, for example, approximately in the longitudinal direction of the lower leg. The reference scale has at its ends fins 4, which may also be designed, for example, as plates or ribs and may protrude at right angles from the reference scale . In one embodiment, the fins 4 advantageously have colored upper sides and undersides. For example, the upper sides may be colored red, and the undersides colored green, or the outer sides, i.e., the upper side of the upper fin and the underside of the lower fin, may be colored red, and the inner sides colored green. Consequently, the fins 4 may serve as an angle-determining (or setting) device, in order to set a viewing direction perpendicular to the reference scale. Consequently, a camera 3 can be positioned at right angles to the reference scale, by checking whether the colored inner or outer sides of the fins 4 are detected. Accordingly, in FIG. 1 the position B is not at right angles to the reference scale, since the camera detects the colored upper side or outer side of the upper fin and the colored upper side or inner side of the lower fin 4. By appropriate adjustment, the camera 3 can be adjusted into the position A, in which the viewing direction extends perpendicularly with respect to the reference scale 2. Consequently, the optical axis 5 of the camera 3 extends perpendicularly with respect to the reference scale 2 and through its center point. The reference scale has a reference zone of a known reference length, which is advantageously formed by the distance of the fins 4 from one another.

A digital camera, for example a CCD camera, is advantageously used as the camera. As mentioned above, one or more cameras can be used according to the present invention.

The positioning of the camera 3 is performed in two directions, advantageously at least essentially perpendicular to one another, about the stump 1 of the lower leg. The stump of the lower leg is advantageously illuminated and recorded in front of a dark background, so that the following determination of the contour line of the stump of the lower leg as a contrast on the image is facilitated. The actual profile of the contour lines, lying in three-dimensional space, is in this case still not known from the projected images of the contour lines in the images. In particular, it is not known here at what distance the contour line lies from the camera 3.

With adequate contrast, the contour lines can be ascertained from the images by image data processing, in which, for example, differences of adjacent pixels are formed. Such edge detection techniques are known, for example, from automatic focusing systems.

Since the reference scale 2 extends perpendicularly with respect to the optical axis of the camera 3, the reference length can be used directly for scaling the image recorded by the camera 3. A scaling is consequently known for the reference plane r1 extending perpendicularly with respect to the optical axis 5 and through the reference zone.

The camera 3 is subsequently adjusted, according to FIG. 5, into a second position D, which likewise lies perpendicular to the reference scale 2. The adjustment is consequently performed without changing the reference scale 2 with the aid of the fins 4. Consequently, the optical axis of the camera in the second measuring position also lies perpendicular to the reference scale 2, but not perpendicular to the reference plane r1 of the first measurement. The second reference plane r2, within which the axis of the reference scale 2 in turn lies, can be defined by the viewing direction or optical axis of the camera 3 in the second camera position D. Consequently, two or more images can be recorded in different (at least two) camera positions, there being formed in each case reference planes in which the axis of the reference scale 2 lies and which respectively lie perpendicularly with respect to the optical axes of the camera.

Figure 2:
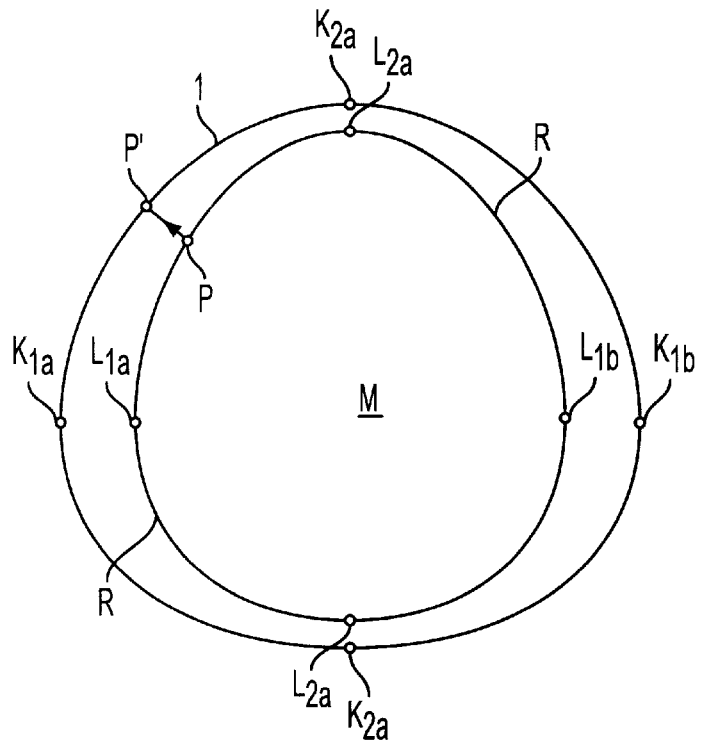
FIG. 2 shows a sectional view of the stump of a lower leg through the contour lines, with the reference model depicted.

FIG. 2 shows a section through the stump 1 of a lower leg in a plane which extends through the two camera positions A, D. A reference model R is used to simulate the outer surface of the lower leg region 1. The reference model can in this case be individually shaped for the body region respectively considered, so that the approximate shaping of the respective body region, for example, of the stump 1 of a lower leg, is already reproduced approximately by the reference model R. According to one embodiment of the invention, the reference model R is subsequently adapted to the actual profile of the outer surface of the stump of the lower leg on the basis of the images recorded by the camera. For this purpose, according to one embodiment of the invention, the actual contour lines K1 and K2 of the outer surface of the lower leg region 1 are determined from the projected images of the contour lines in the images, and the reference model is adapted to the contour lines K1 and K2. It is problematical here that the actual profile of the contour lines K1 and K2 in three-dimensional space is not yet known from the projected images of the contour lines and first has to be determined with the aid of the reference model R. Consequently, the reference model R serves both for determining the contour lines K1 and K2 and for simulating an individual model of the stump 1 of the lower leg on the basis of the contour lines K1 ad K2.

Figure 4:
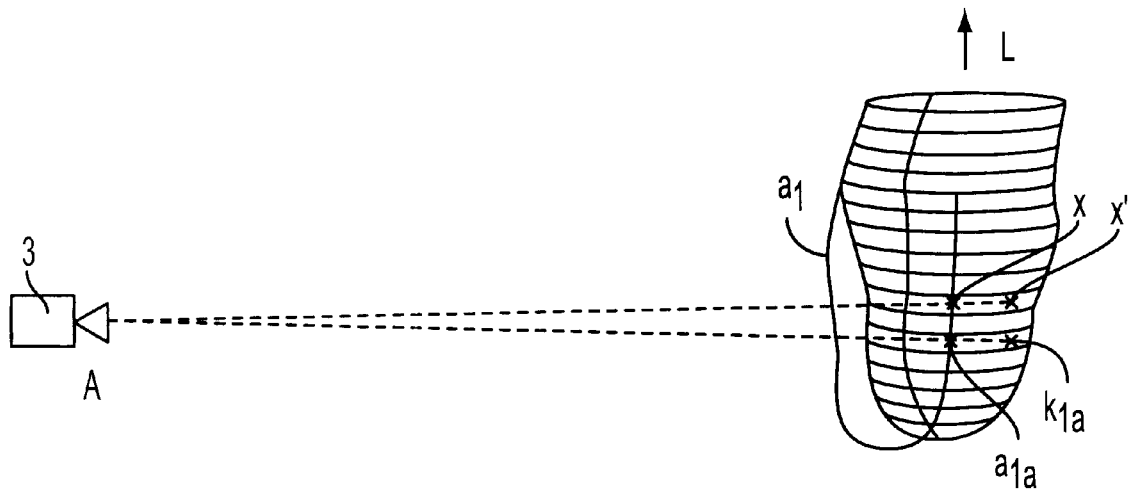
FIG. 4 shows a diagram to illustrate the projection of a reference plane onto a three-dimensional model.
Figure 5:
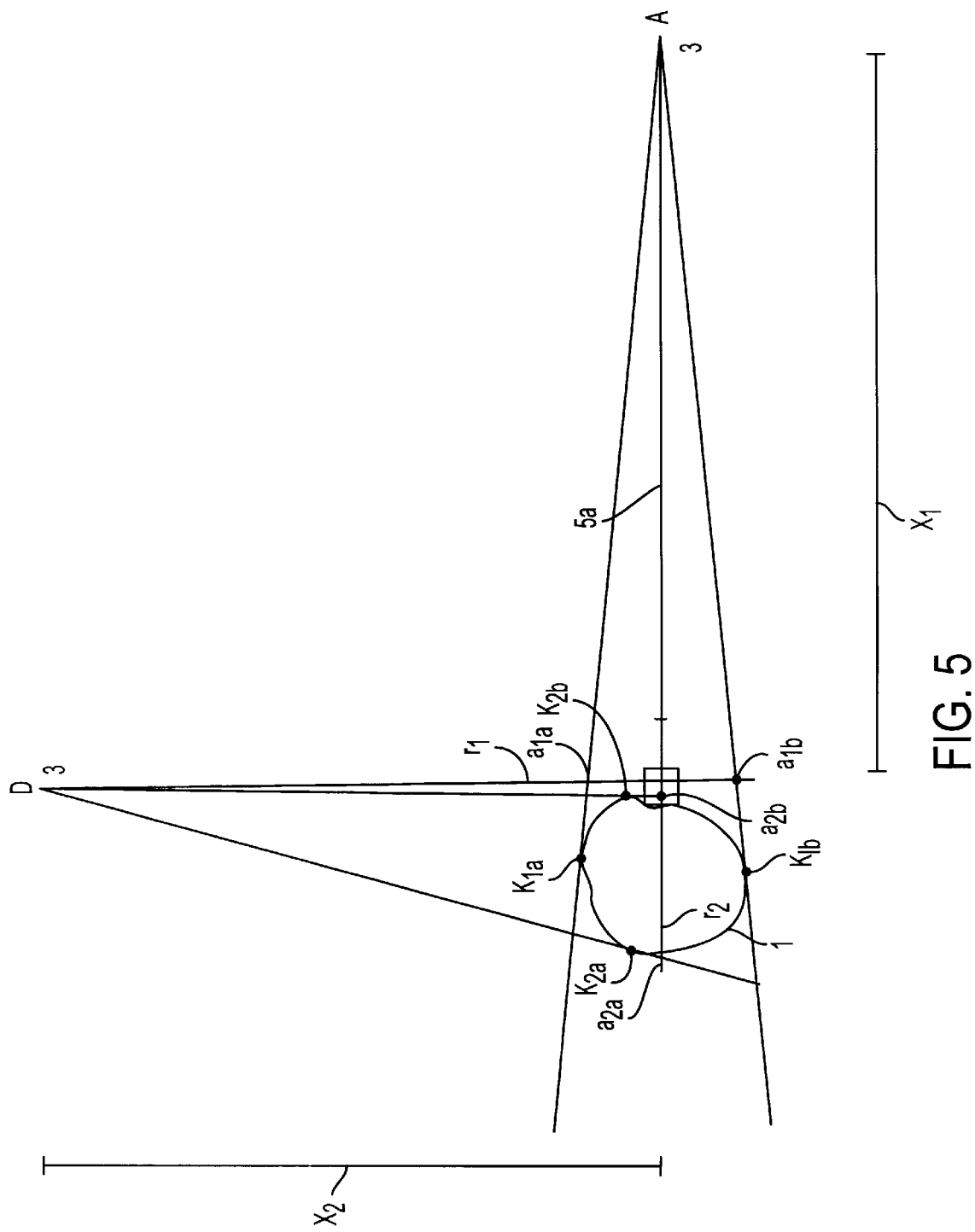
FIG. 5 shows a sectional representation of FIG. 4 through the camera points.

As shown in FIGS. 4 and 5, distances of the reference object 2 from the respective camera positions can be ascertained from the length of the reference zone and the projected images of the reference zone on the images as a first reference distance X1 and a second reference distance X2. A contour line K1, K2, extending in three-dimensional space, can be determined for each image from the reference distance X1, X2 and the projected image of the contour line on the basis of a previously stored reference model R, and an individual model M of the body region 1 can be ascertained from the contour lines K1, K2 and the reference model R.

Since the camera positions A, D are advantageously offset essentially in relation to one another by 90° in the plane shown in FIG. 5, the optical axes 5a, 5b of the camera essentially lie approximately in the reference planes r2, r1 of the respective other position. Such an arrangement is not necessary, however, since the camera positions do not have to be offset by exactly 90° in relation to one another. In principle, it is merely necessary to record two images in camera positions differing from one another.

Figure 3:
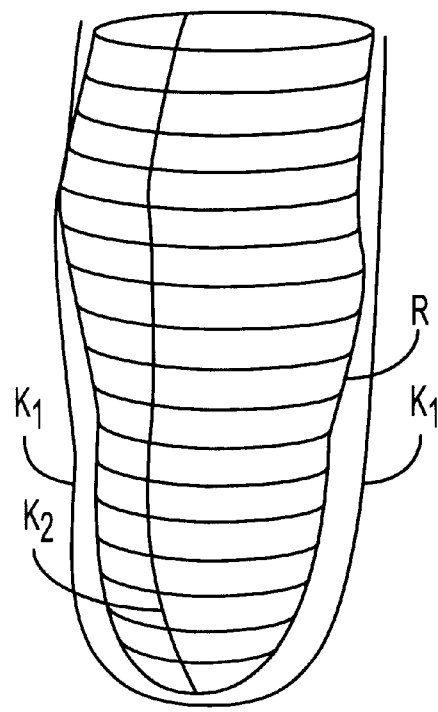
FIG. 3 shows a reference model with contour lines.

FIG. 3 shows the principle according to one embodiment of the invention of using a reference model R which is to be adapted to contour lines K1, K2.

The determination of an individual model is illustrated with respect to FIGS. 4 and 5, with FIG. 5 showing a sectional view of FIG. 4 through one optical axis. According to the embodiment of the invention as shown in FIGS. 4 and 5, the projected images of the contour points K1a, K1b, K2a, K2b are advantageously firstly related to the respective reference planes r1, r2, as is shown for both camera positions. Accordingly, contour line projections a1a, a1b, a2a, a2b are formed in the respective reference planes r1, r2. In these reference planes, the scaling by the reference length of the reference zone is known. In FIG. 4, reference letters X and a1a indicate the intersection of contour projection a1 with an optical axis. Reference letters X' and K1a indicate contour line points of the reference model. Subsequently, as shown in FIG. 5, the individual points a1a, a1b, a2a, a2b of the contour line projections have to be adapted to the contour line points K1a, K1b, K2a, K2b of the lower leg region.

Shown in FIG. 5 in this respect is, firstly, a section through the stump 1 of the lower leg in the plane which is formed by the optical axes 5a, 5b. For the calculation of the contour line points in the further planes, an analogous procedure can subsequently be followed, the camera points A, D respectively lying in these planes. Subsequently, the longitudinal extent of the stump of the lower leg in the direction L in FIG. 4 can be adapted to the scaling of the reference length.

Although the invention has been described above by reference to certain embodiments, the invention is not limited to the embodiments described above. Modifications and variations of the embodiments described above will occur to those skilled in the art, in light of the above teachings. The scope of the invention is defined with reference to the following claims.

German Patent Application No. 199 16 978.0, filed Apr. 15, 1999, including the specification, the drawings, the claims, and the abstract, upon which this application is based, is incorporated herein by reference in its entirety.

What is claimed is:

1. A method of measuring a body region of a human body, comprising:
   arranging in a fixed spatial relationship with the body region a reference object, having a reference zone of a previously known length and an angle-determining device;
   arranging a camera in a first camera position in a first viewing direction, perpendicular to the reference zone, to view the body region with the reference object;
   recording a first image;
   arranging a camera in a second camera position, in a second viewing direction, perpendicular to the reference zone, to view the body region with the reference object;
   recording a second image;
   determining first and second reference distances, which correspond to distances of the reference object from the first and second camera positions, from the length of the reference zone and the projected images of the reference zone on the images;
   determining a contour line exending in three-dimensional space for each image from said reference distances on the oasis of a previously stored reference model; and
   determining an individual model of the body region from said contour lines and said reference model.

2. The method as claimed in claim 1, further comprising:
   defining a reference plane in which the reference zone lies and which extends perpendicularly with respect to the viewing direction of the camera for each camera position;
   determining a contour line projection, which corresponds to a projection of the contour line onto the reference plane for each camera position from said reference distances and a projected image of a contour line obtained from the first and second images; and
   forming said individual model of the body region from said contour line projections, said reference distances, and said reference model.

3. The method as claimed in claim 1, further comprising:
   applying a contrast-improving coating over the body region.

4. The method as claimed in claim 1, further comprising:
   determining a length of the individual model extending perpendicularly with respect to said viewing directions from a comparison of the reference zone with a distance between two points of the body region.

5. The method as claimed in claim 4, wherein at least one of said points is one end of the body region.

6. The method as claimed in claim 4, wherein at least one of said points is a location marked on a coating applied to the body region.

7. The method as claimed in claim 1, wherein said determining an individual model of the body region comprises:
   determining an individual model of the body region from said contour lines, said reference model, and projected images of locations or subregions of the body region which can be detected in at least one of the projected images of the body region.

8. The method as claimed in claim 1, wherein the reference object is fastened on the body region.

9. The method as claimed in claim 1, wherein the reference object has two markings at a known distance, which fix the reference zone.

10. The method as claimed in claim 1, wherein said camera is arranged in said first and second viewing direction with a visual angle-determining device having at least one projection extending perpendicularly with respect to the reference zone.

11. The method as claimed in claim 10, wherein the angle-determining device has two projections which are spaced apart from one another, extend perpendicularly with respect to the reference zone, and between them form the reference zone.

12. The method as claimed in claim 10, wherein said projection has a colored surface.

13. The method as claimed in claim 1, wherein the same camera is used in said first and second camera positions.

14. The method as claimed in claim 1, wherein a stump of a limb is measured as the body region.

15. The method as claimed in claim 14, wherein said stump is a stump of a lower leg.

16. The method as claimed in claim 1, wherein a limb is measured as the body region.

17. The method as claimed in claim 1, wherein a foot is measured as the body region.

18. A method of measuring a body region of a human body, comprising:
   arranging a reference object with a reference zone of a previously known length and an angle-determining device in a fixed spatial relationship with the body region;
   arranging a camera with the angle-determining device in a first viewing direction, perpendicular to the reference zone, in a first camera position, wherein the camera picks up the body region with the reference object and a first image is recorded;
   arranging a camera with the angle-determining device in a second viewing direction, perpendicular to the reference zone, in a second camera position, wherein the camera picks up the body region with the reference object, and a second image is recorded;
   determining the distances of the reference object from the camera positions from the length of the reference zone and the projected images of the reference zone on the images as a first reference distance and second reference distance;
   determining a contour line, extending in three-dimensional space, for each image from the reference distance on the basis of a previously stored reference model; and
   determining an individual model of the body region from the contour lines and the reference model.

19. A method of fitting a patient with a prothesis or an orthesis, comprising:
   measuring a body region of the patient according to the method claimed in claim 1; and
   constructing a prosthesis or an orthesis from the individual model of the body region.

20. A method as claimed in claim 19, further comprising:
   communicating electronic data corresponding to the individual model to a location remote from the measuring location.

21. The method according to claim 1, wherein the determined contour line is further determined on the basis of a projected image of a contour line that is obtained from the first and second images.

* * * * *